(12) United States Patent
Shin et al.

(10) Patent No.: US 10,710,961 B2
(45) Date of Patent: Jul. 14, 2020

(54) METHOD FOR PREPARING INTERMEDIATE OF 4-METHOXYPYRROLE DERIVATIVE

(71) Applicant: Daewoong Pharmaceutical Co., Ltd., Gyeonggi-do (KR)

(72) Inventors: Jeong-Taek Shin, Gyeonggi-do (KR); Jeong-Hyun Son, Gyeonggi-do (KR); Deok Ki Eom, Gyeonggi-do (KR); Chun Ho Lee, Seoul (KR)

(73) Assignee: Daewoong Pharmaceutical Co., Ltd., Gyeonggi-do (KR)

( * ) Notice: Subject to any disclaimer, the term of this patent is extended or adjusted under 35 U.S.C. 154(b) by 0 days.

(21) Appl. No.: 16/608,910

(22) PCT Filed: May 31, 2018

(86) PCT No.: PCT/KR2018/006188
§ 371 (c)(1),
(2) Date: Oct. 28, 2019

(87) PCT Pub. No.: WO2018/221971
PCT Pub. Date: Dec. 6, 2018

(65) Prior Publication Data
US 2020/0181079 A1 Jun. 11, 2020

(30) Foreign Application Priority Data

May 31, 2017 (KR) .................. 10-2017-0067646

(51) Int. Cl.
*C07D 207/36* (2006.01)
(52) U.S. Cl.
CPC .................. *C07D 207/36* (2013.01)
(58) Field of Classification Search
CPC .................................................. C07D 207/36
See application file for complete search history.

(56) References Cited

U.S. PATENT DOCUMENTS

| | | | |
|---|---|---|---|
| 6,307,059 | B1 | 10/2001 | Chang et al. |
| 8,048,909 | B2 | 11/2011 | Kajino et al. |
| 8,383,853 | B2 | 2/2013 | Fischer et al. |
| 9,388,133 | B2 | 7/2016 | Lan et al. |
| 10,100,010 | B1 | 10/2018 | Lee et al. |
| 10,336,695 | B2 | 7/2019 | Kim et al. |

FOREIGN PATENT DOCUMENTS

| | | |
|---|---|---|
| EA | 200000900 A1 | 2/2001 |
| EP | 714895 A1 | 6/1996 |
| KR | 2015-0084974 A | 7/2015 |
| KR | 10-1613245 B1 | 4/2016 |
| KR | 2017-0111170 A | 10/2017 |
| RU | 95121094 | 11/1997 |
| UA | 86467 C2 | 4/2009 |
| WO | WO-2006/025716 A1 | 3/2006 |
| WO | WO-2006/036024 A1 | 4/2006 |
| WO | WO-2007/072146 A1 | 6/2007 |
| WO | WO-2016/175555 A2 | 11/2016 |

OTHER PUBLICATIONS

Gabbutt et al. "A facile route to pyrroles, isoindoles and hetero fused analogues" J. Chem. Soc., Perkin Trans. 1, 2002, 2799-280.*
Decision of Grant in RU Application No. 2019135240 dated Mar. 23, 2020, 22 pages.
Search Report and Written Opinion in International Application No. PCT/KR2018/006188 dated Sep. 7, 2018, 13 pages.

* cited by examiner

*Primary Examiner* — Joseph R Kosack
(74) *Attorney, Agent, or Firm* — Marshall, Gerstein & Borun LLP

(57) ABSTRACT

The present invention relates to a method for preparing intermediates of 4-methoxypyrrole derivatives. The preparation method according to the present invention has advantages that a high-temperature reaction is not required as a whole, inexpensive and non-explosive reagents are used instead of (trimethylsilyl)diazomethane, and further an intermediate of 4-methoxy pyrrole derivatives can be prepared as a whole at a high yield.

15 Claims, No Drawings

METHOD FOR PREPARING INTERMEDIATE OF 4-METHOXYPYRROLE DERIVATIVE

TECHNICAL FIELD

The present invention relates to a method for preparing intermediates used in the preparation of 4-methoxypyrrole derivatives.

BACKGROUND OF ART

Gastrointestinal track ulcers, gastritis, and reflux esophagitis occur while the balance between aggressive factors (e.g., gastric acid, *Helicobacter pylori* pepsin, stress, alcohol and tobacco) and protective factors (e.g., gastric mucosa, bicarbonate, prostaglandins, the degree of blood supply, etc.) is destroyed. Therefore, a therapeutic agent for gastrointestinal damage such as gastrointestinal track ulcer, gastritis and reflux esophagitis is divided into a drug for inhibiting the aggressive factors and a drug for enhancing the protective factors.

Meanwhile, it is reported that gastrointestinal track ulcers, gastritis and reflux esophagitis occur ulcers even without an increase in secretion of gastric acid. Thus, as much as the aggressive factor increases, a reduction in protective factors due to a pathological change of the gastric mucosa is thought to play an important role in the occurrence of gastric ulcers. Therefore, in addition to drugs for inhibiting the aggressive factor, drugs for enhancing the protective factors are used for the treatment of gastrointestinal ulcer and gastritis. As the drugs for enhancing protective factors, mucosal protective drugs which are attached to the ulcer site to form a physicochemical membrane, drugs that promote the synthesis and secretion of mucus have been known.

On the other hand, *Helicobacter pylori* (*H. pylon*), which is a bacteria present in the stomach, has been known to cause chronic gastritis, gastric ulcer, duodenal ulcer and the like, and a number of patients with gastrointestinal damages are infected with *H. pylori*. Therefore, these patients should take antibiotics such as clarithromycin, amoxicillin, metronidazole and tetracycline, together with anti-ulcer agents such as a proton pump inhibitor, or a gastric pump antagonist. Consequently, various side effects have been reported.

Therefore, there is a need to develop anti-ulcer drugs which inhibit the secretion of gastric acid (e.g., proton pump inhibitory activity) and enhance protective factors (e.g., an increase in mucus secretion) and at the same time have disinfectant activity against *H. pylori*.

In this connection, Korean Patent No. 10-1613245 discloses that a 4-methoxypyrrole derivative or a pharmaceutically acceptable salt thereof has excellent anti-ulcer activity (i.e., proton pump inhibitory activity, etc.) and disinfectant activity against *H. pylori*, and thus can be effectively used for the prevention and treatment of gastrointestinal damage due to gastrointestinal track ulcer, gastritis, reflux esophagitis or *Helicobacter pylori*.

In the preparation of the 4-methoxypyrrole derivative described in the above patent, the following compound is prepared as an intermediate.

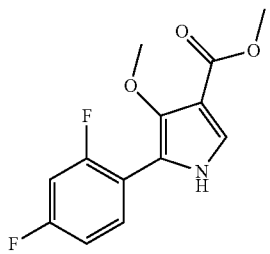 [SMILES: COC(=O)c1c[nH]c(-c2ccc(F)cc2F)c1OC]

According to the description of the above patent, the intermediate is prepared from 2,4-difluorophenylglycine, and the preparation method consists of four steps in total (Steps (8-1) to (8-3) of Example 8 described in Korean Patent No. 10-1613245). However, according to the preparation method of the above patent, the total yield is as low as 9.0%, a high-temperature reaction is required as a whole, and thus expensive equipment is required. Especially, (trimethylsilyl)diazomethane is used as a reactant, but this reagent is not only expensive but also explosive and thus is not suitable for industrial mass production.

Given the above circumstances, the present inventors have conducted intensive studies on a new preparation method capable of preparing the above intermediate. As a result, the inventors have found a preparation method in which a high-temperature reaction is not required as a whole as in the preparation method described later, and inexpensive, non-explosive reagent is used instead of (trimethylsilyl)diazomethane, and further, the yield is improved as a whole, thereby completing the present invention.

DETAILED DESCRIPTION OF THE INVENTION

Technical Problem

It is an object of the present invention to provide a method for preparing an intermediate which can be usefully used in the preparation of 4-methoxypyrrole derivatives.

Technical Solution

In order to achieve the above object, the present invention provides a preparation method as shown in the following Reaction Scheme 1, and more specifically, the preparation method comprises the steps of:

1) reacting a compound represented by the following Chemical Formula 1-1 with a compound represented by the following Chemical Formula 1-2 to prepare a compound represented by the following Chemical Formula 1-3;

2) reacting a compound represented by the following Chemical Formula 1-3 with acetic anhydride in the presence of any one base selected from the group consisting of potassium carbonate, potassium hydrogen carbonate, sodium carbonate, sodium hydrogen carbonate, and cesium carbonate to prepare a compound represented by the following Chemical Formula 1-4;

3) reacting a compound represented by the following Chemical Formula 1-4 in the presence of a base to prepare a compound represented by the following Chemical Formula 1-5; and 4) reacting a compound represented by the following Chemical Formula 1-5 with dimethyl sulfate in the presence of a base to prepare a compound represented by the following Chemical Formula 1.

[Reaction Scheme 1]

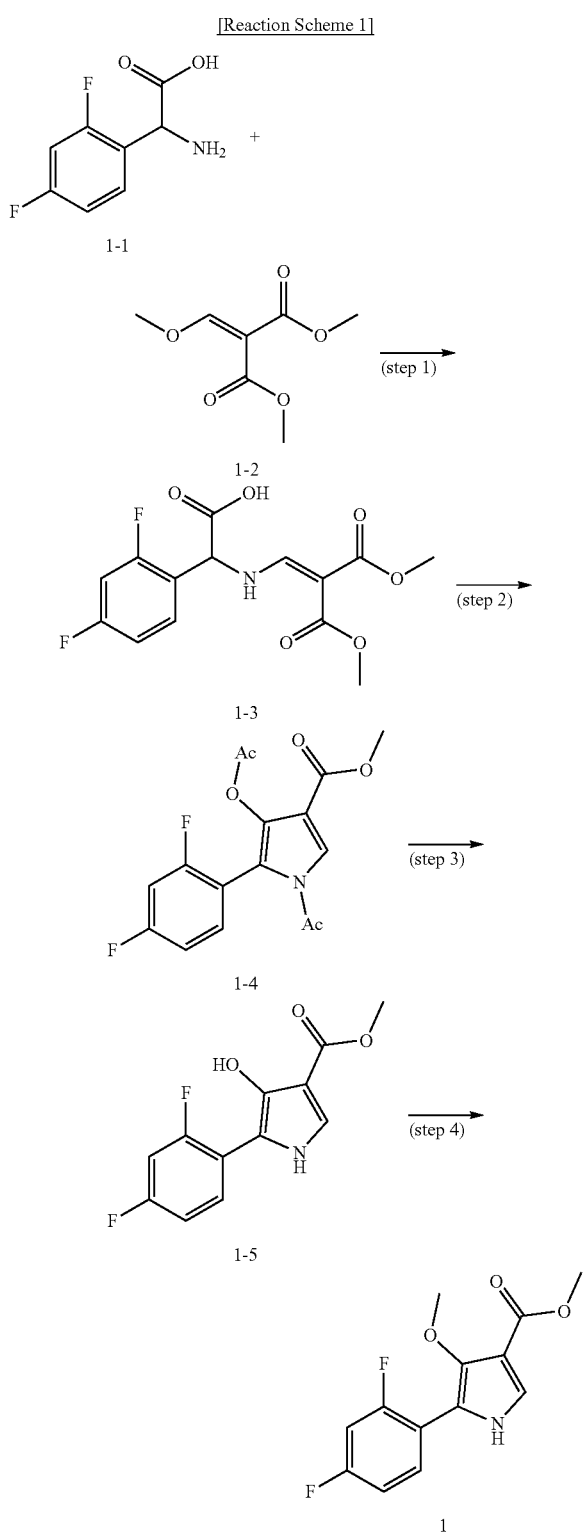

Hereinafter, the present invention will be described in detail for each step.

(Step 1)

The step 1 is a step of reacting a compound represented by the Chemical Formula 1-1 with a compound represented by the Chemical Formula 1-2 to prepare a compound represented by the Chemical Formula 1-3.

Preferably, the molar ratio of the compound represented by the Chemical Formula 1-1 to the compound represented by the Chemical Formula 1-2 is 10:1 to 1:10, more preferably 5:1 to 1:5, and most preferably 3:1 to 1:3.

Preferably, as a solvent for the above reaction, an alcohol having from 1 to 4 carbon atoms is used. More preferably, the solvent for the reaction is methanol, ethanol, propanol, butanol, or tert-butanol.

In addition, the reaction is preferably carried out in the presence of a base. As the base, sodium acetate, lithium acetate, or potassium acetate can be used, and preferably, sodium acetate is used.

Preferably, the reaction is carried out at 60° C. to 100° C. When the reaction temperature is less than 60° C., there is a problem that the production yield is lowered. When the reaction temperature exceeds 100° C., the production yield does not substantially increase. More preferably, the reaction is carried out at 70° C. to 90° C.

Preferably, the reaction is carried out for 30 minutes to 5 hours. When the reaction time is less than 30 minutes, there is a problem that the reaction does not proceed sufficiently and thus the production yield is lowered. When the reaction time exceeds 5 hours, the production yield does not substantially increase. More preferably, the reaction is carried out for 1 to 3 hours.

On the other hand, after the reaction is completed, a step of purifying a compound represented by the Chemical Formula 1-3 may be included, if necessary. Preferably, the purification is carried out by crystallizing a compound represented by the Chemical Formula 1-3 from the product of the reaction. As the crystallization solvent, diisopropyl ether can be used. Preferably, the product of the reaction is cooled to 5 to 30° C., and then diisopropyl ether is added thereto and stirred for 10 minutes to 2 hours.

(Step 2)

The step 2 is a step of reacting a compound represented by the Chemical Formula 1-3 with acetic anhydride in the presence of any one base selected from the group consisting of potassium carbonate, potassium hydrogen carbonate, sodium carbonate, sodium hydrogen carbonate, and cesium carbonate to prepare a compound represented by the Chemical Formula 1-4.

Preferably, the molar ratio of the compound represented by the Chemical Formula 1-3 to acetic anhydride is 1:1 to 1:32, and more preferably 1:1 to 1:25. Preferably, the molar ratio of the compound represented by the Chemical Formula 1-3 to the base is 1:1 to 1:10, and more preferably 1:1 to 1:5.

On the other hand, in Korean Patent No. 10-1613245, the compound represented by the Chemical Formula 1-3 is reacted with acetic anhydride in the presence of triethylamine. However, when triethylamine is used, the reaction temperature must be adjusted to about 140° C. Therefore, there is a problem in that not only a high-temperature equipment is required but also the production yield is low.

Thus, in the present invention, it is possible not only to lower the reaction temperature but also to improve the production yield by using the above-mentioned base instead of triethylamine. Preferably, the reaction is carried out at 70 to 100° C. As described above, the reaction can be carried out at a lower temperature than the Korean Patent No. 10-1613245, and the production yield can be increased as in the examples of the present invention described later. Preferably, the molar ratio of the compound represented by the Chemical Formula 1-3 to the base is 1:1 to 1:10.

Preferably, the solvent for the reaction is acetonitrile, or tetrahydrofuran.

Preferably, the reaction is carried out for 30 minutes to 5 hours. When the reaction time is less than 30 minutes, there is a problem that the reaction does not proceed sufficiently and thus the production yield is lowered. When the reaction time exceeds 5 hours, the production yield does not substantially increase. More preferably, the reaction is carried out for 30 minutes to 3 hours.

On the other hand, after the reaction is completed, a step of purifying a compound represented by the Chemical Formula 1-4 may be included, if necessary.

(Step 3)

The step 3 is a step of reacting a compound represented by the Chemical Formula 1-4 in the presence of a base to prepare a compound represented by the Chemical Formula 1-5.

As the base, sodium hydroxide, lithium hydroxide, potassium hydroxide, or barium hydroxide can be used, and preferably, sodium hydroxide can be used. Preferably, the molar ratio of the compound represented by the Chemical Formula 1-4 to the base is 1:1 to 1:10.

Preferably, as a solvent for the reaction, an alcohol having 1 to 4 carbon atoms is used. More preferably, methanol, ethanol, propanol or tert-butanol is used as the solvent for the reaction. Further, it is preferable to use tetrahydrofuran in addition to the above-mentioned solvent.

Preferably, the reaction is carried out at −45 to 5° C. When the reaction temperature is less than −45° C., there is a problem that the production yield is lowered, and when the reaction temperature exceeds 5° C., a side reaction occurs, which is not preferable. More preferably, the reaction is carried out at −35 to 0° C.

Preferably, the reaction is carried out for 3 hours or less. When the reaction time exceeds 3 hours, a side reaction occurs, which is not preferable. More preferably, the reaction is carried out for 2 hours or less.

On the other hand, after the reaction is completed, a step of purifying a compound represented by the Chemical Formula 1-5 may be included, if necessary. Preferably, the purification may include a step of crystallizing a compound represented by the Chemical Formula 1-5 from the product of the reaction. As the crystallization solvent, methanol can be used. Preferably, to the product of the reaction is added methanol at 50 to 70° C. and stirred for 10 minutes to 2 hours.

(Step 4)

The step 4 is a step of reacting a compound represented by the Chemical Formula 1-5 with dimethyl sulfate in the presence of a base to prepare a compound represented by the Chemical Formula 1.

As the base, sodium hydroxide, lithium hydroxide, potassium hydroxide, triethylamine, diisopropylamine, diisopropylethylamine, potassium carbonate, sodium hydrogen carbonate, potassium hydrogen carbonate, cesium carbonate, sodium carbonate, sodium methylate, or potassium butyrate may be used, and preferably, sodium hydroxide is used. In addition, the reaction can be carried out using methyl iodide in the presence of a base.

In Korean Patent No. 10-1613245, the compound represented by the Chemical Formula 1-5 is reacted with (Trimethylsilyl)diazomethane (TMS-diazomethane). However, since TMS-diazomethane is expensive and difficult to handle as an explosive substance, and thus expensive equipment is required. Thus, in the present invention, dimethyl sulfate which does not have a risk of explosion is used, instead of TMS-diazomethane.

Preferably, the molar ratio of the compound represented by the Chemical Formula 1-5 to dimethyl sulfate is 1:1 to 1:10, and more preferably 1:1 to 1:5. Preferably, the molar ratio of the compound represented by the Chemical Formula 1-5 to the base is 1:1 to 1:10, and more preferably 1:1 to 1:5.

Preferably, as the solvent for the reaction, an alcohol having 1 to 4 carbon atoms or a ketone having 3 to 6 carbon atoms may be used. More preferably, the solvent for the reaction is methanol, ethanol, propanol, butanol, tert-butanol, acetone, methyl ethyl ketone, or isobutyl ketone.

Preferably, the reaction is carried out at −5 to 10° C. When the reaction temperature is less than −5° C., there is a problem that the production yield is lowered. When the reaction temperature exceeds 10° C., a side reaction occurs, which is not preferable. More preferably, the reaction is carried out at 0 to 5° C.

Preferably, the reaction is carried out for 30 minutes to 5 hours. If the reaction time is less than 30 minutes, there is a problem that the reaction does not proceed sufficiently and thus the production yield is lowered. When the reaction time exceeds 5 hours, a side reaction occurs, which is not preferable. More preferably, the reaction is carried out for from 1 to 3 hours.

On the other hand, after the reaction is completed, a step of purifying a compound represented by the Chemical Formula 1 may be included, if necessary. Preferably, the purification may include a step of crystallizing a compound represented by the Chemical Formula 1 from the product of the reaction. As the crystallization solvent, ethyl acetate and n-hexane can be used. Preferably, the product of the reaction is stirred at 10 to 40° C. by adding ethyl acetate for 1 minute to 1 hour, and then n-hexane is added thereto to precipitate crystals.

Advantageous Effects

As described above, the preparation method according to the present invention has advantages that a high-temperature reaction is not required as a whole, inexpensive and non-explosive reagents are used instead of (trimethylsilyl)diazomethane, and further an intermediate of 4-methoxypyrrole derivatives can be prepared as a whole at a high yield.

DETAILED DESCRIPTION OF THE EMBODIMENTS

Hereinafter, the present invention will be described in more detail with reference to the following examples. However, the following examples are for illustrative purposes only and are not intended to limit the scope of the present invention thereto.

Example

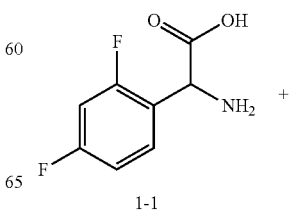

1-1

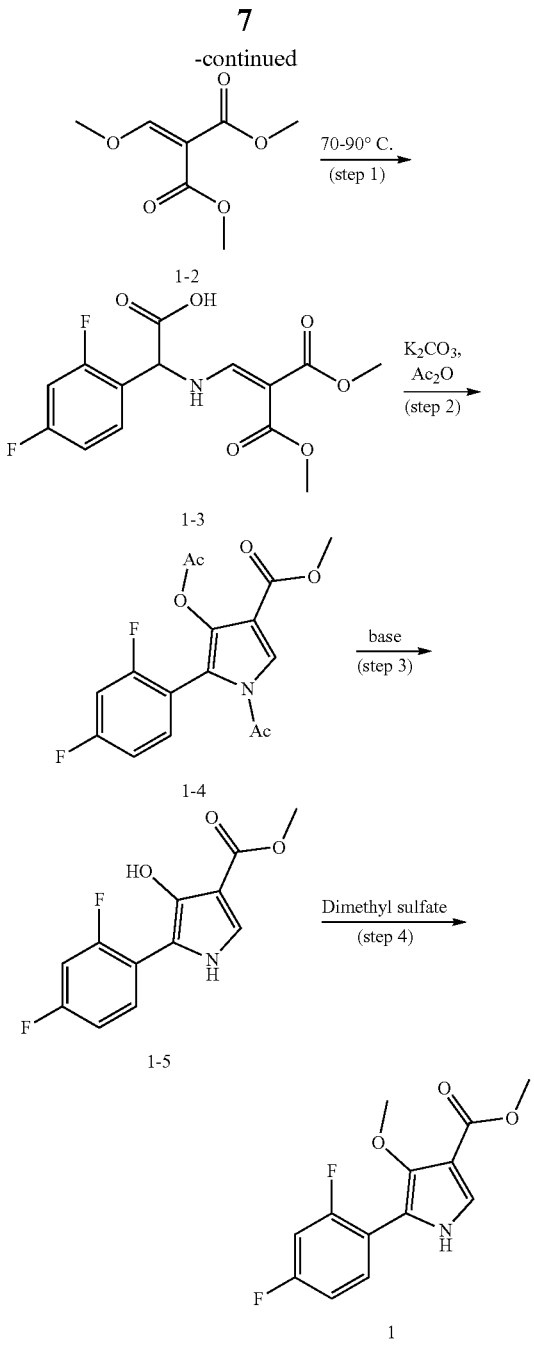

$^1$H-NMR (500 MHz, CDCl$_3$): 8.02-7.99 (m, 1H), 7.45-7.40 (m, 1H), 7.00-6.95 (m, 2H), 5.16 (s, 1H), 3.74 (s, 3H), 3.76 (s, 3H)

(Step 2)

100.0 g of the compound represented by the Chemical Formula 1-3, 125.9 g of potassium carbonate (powder), 2.0 L of acetonitrile, and 516.8 mL of acetic anhydride were sequentially added to a flask, and then refluxed at an external temperature of 87-93° C. for 30 minutes to complete the reaction. Then, the internal temperature was cooled to 20 to 30° C. 500.0 mL of distilled water was added and stirred for 10 minutes to separate the organic layer. The extracted organic layer was concentrated under reduced pressure at an external temperature of 97 to 103° C. 1.0 L of ethyl acetate was added to the concentrated residue, and then stirred. Ammonium chloride solution was added thereto, and then stirred at 20 to 30° C. for 10 minutes to separate an organic layer. Distilled water was added to the organic layer and the pH was adjusted to 9.3 using ammonium hydroxide (25-28%). The organic layer was separated by stirring at 20 to 30° C. for 10 minutes. Distilled water was added to the organic layer and the pH was adjusted to 10.0~10.5 using ammonium hydroxide (25~28%). The organic layer was separated, and then concentrated under reduced pressure at an external temperature of 57 to 63° C. Tetrahydrofuran was added to the concentrated residue, stirred at 20 to 30° C. for 10 minutes, and then concentrated under reduced pressure at an external temperature of 57 to 63° C. to prepare a compound represented by the Chemical Formula 1-4 and then used in the following step 3.

$^1$H-NMR (400 MHz, DMSO): 8.18 (s, 1H), 7.33 (m, 2H), 7.16 (m, 1H), 3.81 (s, 3H), 2.64 (s, 3H), 2.15 (s, 3H)

(Step 3)

260.0 mL of tetrahydrofuran was added to the compound represented by the Chemical Formula 1-4 prepared in step 2, and then stirred at 20 to 30° C. for 10 minutes. The internal temperature was then cooled to −35 to −10° C. The previously prepared sodium hydroxide solution (containing 15.4 g of sodium hydroxide and 65.0 mL of methanol) was added slowly thereto while maintaining an internal temperature of −10 to 0° C. Immediately after completion of the addition, the completion of the reaction was confirmed. Then, 1N—HCl solution was slowly added thereto to adjust the pH to 6.9 to 7.1 at an internal temperature of −5 to 20° C. Ethyl acetate and distilled water were added thereto, and then stirred at 20 to 30° C. for 10 minutes. The organic layer was separated and concentrated under reduced pressure at an external temperature of 50 to 55° C. Methanol was added to the concentrated residue and stirred at an internal temperature of 60 to 65° C. for 10 minutes. The internal temperature was cooled to 10 to 20° C. to precipitate crystals. Purified water was added thereto and stirred at an internal temperature of 20 to 25° C. for 1 hour to further precipitate crystals. Filtration was carried out using a filter under reduced pressure and the filtrate was washed with 50% aqueous methanol solution. The resulting solid was dried under reduced pressure to produce 38.1 g of the compound represented by the above formula (1-5) (yield: 49.6% (including steps 2 and 3)).

$^1$H-NMR (500 MHz, CDCl$_3$): 8.80 (s, 1H), 8.17-8.12 (m, 2H), 7.13 (d, 1H), 6.95 (t, 1H), 6.86-6.83 (m, 1H), 3.88 (s, 3H)

(Step 4)

34.7 g of sodium hydroxide and 1.43 L of methanol were sequentially added to a flask, and then cooled to 0 to 5° C., to which 100.0 g of the previously prepared compound represented by the Chemical Formula 1-5 was added. 150.0

(Step 1)

100.0 g of 2,4-difluorophenylglycine (Chemical Formula 1-1), 93.1 g of dimethyl 2-(methoxymethylene)malonate (Chemical Formula 1-2), 43.9 g of sodium acetate and 600.0 mL of methanol were sequentially added to a flask. The mixture was refluxed at an external temperature of 70 to 90° C. for 2 hours to complete the reaction. Then, the internal temperature was cooled to 20 to 30° C. using an ice bath. Diisopropyl ether was added thereto, and the internal temperature was cooled to 10 to 15° C., and the mixture was stirred for 1 hour and crystallized. The crystals were filtered, and the filtrate was washed with diisopropyl ether. The resulting solid was dried under reduced pressure to obtain 153.8 g of the compound represented by the Chemical Formula 1-3 (yield: 90.0%).

mL of dimethyl sulfate was slowly added thereto at an internal temperature of 0 to 5° C. The mixture was stirred for 1 hour and the completion of the reaction was confirmed. Then, the pH was adjusted to 6.9 to 7.1 using 1N—HCl. It was concentrated under reduced pressure at an external temperature of 50 to 55° C. 1.0 L of ethyl acetate was added to the concentrated residue, and then stirred at 20 to 30° C. for 10 minutes. After cooling to 10~20° C., the pH range was adjusted to 7.0~8.0 with aqueous sodium bicarbonate solution while maintaining the same temperature range. The organic layer was extracted, dried over anhydrous magnesium sulfate, and then concentrated under reduced pressure to an external temperature of 50 to 55° C. Ethyl acetate and n-hexane were added to the concentrated residue to precipitate crystals. After cooling to 0~5° C., stirring was carried out for 1 hour, the crystals were filtered, and the filtered crystals were washed with n-hexane. The resulting solid was dried under reduced pressure to obtain 58.1 g of the compound represented by the Chemical Formula 1 (yield: 55.0%).

$^1$H-NMR (500 MHz, CDCl$_3$): 8.78 (s, 1H), 8.12 (m, 1H), 7.30 (d, 1H), 6.95 (t, 1H), 6.88 (t, 1H), 3.87 (s, 3H), 3.85 (s, 3H)

Comparative Example

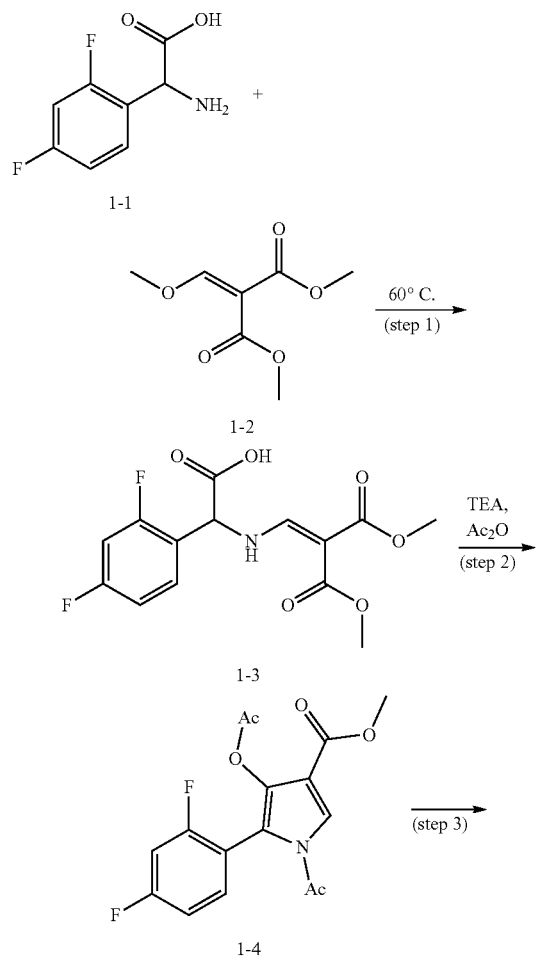

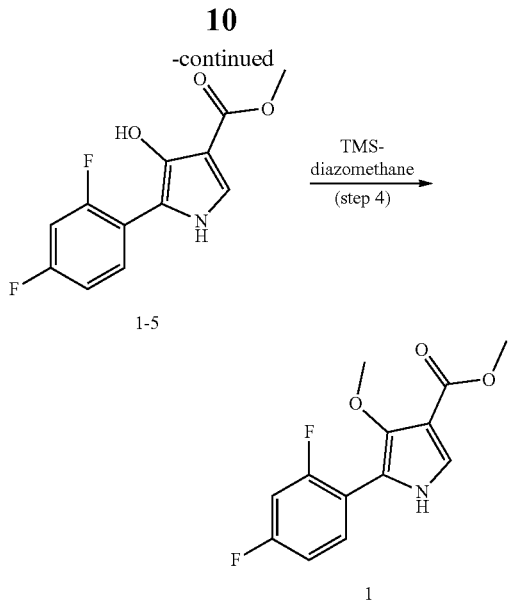

The preparation method was carried out as follows in the same manner as in steps 8-1 to 8-3 of Example 8 of Korean Patent No. 10-1613245.

(Step 1)

2,4-Difluorophenylglycine (Chemical Formula 1-1, 150.0 g, 801.5 mmol), dimethyl 2-(methoxymethylene)malonate (Chemical Formula 1-2, 126.9 g, 728.6 mmol), and sodium acetate (65.8 g, 801.5 mmol) were added to methanol (800.0 ml), and then refluxed at 60° C. for 4 hours. The reaction mixture was cooled to room temperature, and concentrated under reduced pressure to remove about 70% of methanol, and then filtered. The resulting solid was dried under reduced pressure to produce 190.0 g of the compound represented by the Chemical Formula 1-3 (yield: 79.2%).

$^1$H-NMR (500 MHz, CDCl$_3$): 8.02-7.99 (m, 1H), 7.45-7.40 (m, 1H), 7.00-6.95 (m, 2H), 5.16 (s, 1H), 3.74 (s, 3H), 3.76 (s, 3H)

(Step 2)

Acetic anhydride (1731.2 ml) and triethylamine (577.1 ml) were added to the compound represented by the Chemical Formula 1-3 (190.0 g, 577.1 mmol) prepared in step 1. The reaction mixture was refluxed at 140° C. for 30 minutes and then cooled to 0° C. To the reaction mixture, ice water (577.1 ml) was added at 0° C., stirred at room temperature for 1 hour and then extracted with ethyl acetate. The obtained extract was dried over anhydrous magnesium sulfate and then concentrated under reduced pressure. The resulting compound was filtered using a silica gel to remove a solid, and then concentrated under reduced pressure to prepare the compound represented by the Chemical Formula 1-4, which was then used in the following step 3.

(Step 3)

Tetrahydrofuran (140.0 ml) and water (120.0 ml) were added to the resulting residue, cooled to 0° C., followed by addition of sodium hydroxide (46.17 g, 1154.2 mmol). The reaction mixture was stirred at 0° C. for 30 minutes, neutralized using 1N hydrochloric acid aqueous solution and then extracted with ethyl acetate. The obtained extract was dried over anhydrous magnesium sulfate, and then concentrated under reduced pressure. The resulting residue was purified by silica gel column chromatography (ethyl acetate: n-hexane=1:4 (v/v)) to produce 22.0 g of the compound represented by the Chemical Formula 1-5 (yield: 15.1%) (including steps 2 and 3).

$^1$H-NMR (500 MHz, CDCl$_3$): 8.80 (s, 1H), 8.17-8.12 (m, 2H), 7.13 (d, 1H), 6.95 (t, 1H), 6.86-6.83 (m, 1H), 3.88 (s, 3H)

(Step 4)

The compound represented by the Chemical Formula 1-5 (22.0 g, 86.9 mmol) prepared in step 3 was dissolved in tetrahydrofuran (434.5 ml) and methanol (173.9 ml). (Trimethylsilyl)diazomethane (2.0M diethyl ether solution, 173.8 ml) was added to the reaction mixture and then stirred at room temperature for 48 hours. Water was added to the reaction mixture, and extracted with ethyl acetate. The obtained extract was dried over anhydrous magnesium sulfate, and then concentrated under reduced pressure. The resulting residue was purified by silica gel column chromatography (ethyl acetate:n-hexane=1:4 (v/v)) to produce 18.1 g of the compound represented by the Chemical Formula 1 (yield: 75.3%).

$^1$H-NMR (500 MHz, CDCl$_3$): 8.78 (s, 1H), 8.12 (m, 1H), 7.30 (d, 1H), 6.95 (t, 1H), 6.88 (t, 1H), 3.87 (s, 3H), 3.85 (s, 3H)

Comparison of Examples and Comparative Examples

The yields of the preparation methods of the Example and Comparative Example are shown in Table 1 below.

TABLE 1

|  | Example | Comparative Example |
|---|---|---|
| Step 1 | 90.0% | 79.2% |
| Steps 2 & 3 | 49.6% | 15.1% |
| Step 4 | 55.0% | 75.3% |
| Total yield | 24.6% | 9.0% |

As shown Table 1, in steps 1 to 3, the yield of Example according to the present invention was improved compared to that of Comparative Example. Especially in steps 2 and 3, the yield of Example according to the present invention was improved by about 3.3 times compared to that of Comparative Example. Further, in step 2, in the present invention, a reaction temperature of about 90° C. was applied, whereas in Comparative Example, a reaction temperature of about 140° C. was applied. Therefore, the present invention has an advantage that a relatively low reaction temperature can be applied.

In addition, in step 4, Example according to the present invention showed a slight decrease in yield relative to Comparative Example. However, Comparative Example used (trimethylsilyl)diazomethane which is an expensive and explosive reactant, whereas Example used a safe reactant which is relatively inexpensive and non-explosive, which is advantageous for industrial production.

In addition, Example according to the present invention showed about 2.7 times improved yield compared to Comparative Example, which confirms that the efficiency of the production process was improved even while using a reactant which is relatively inexpensive, without risk of explosion.

What is claimed is:

1. A method for preparing a compound represented by the following Chemical Formula 1, comprising the steps of:
  1) reacting a compound represented by the following Chemical Formula 1-1 with a compound represented by the following Chemical Formula 1-2 to prepare a compound represented by the following Chemical Formula 1-3;
  2) reacting a compound represented by the following Chemical Formula 1-3 with acetic anhydride in the presence of any one base selected from the group consisting of potassium carbonate, potassium hydrogen carbonate, sodium carbonate, sodium hydrogen carbonate, and cesium carbonate to prepare a compound represented by the following Chemical Formula 1-4;
  3) reacting a compound represented by the following Chemical Formula 1-4 in the presence of a base to prepare a compound represented by the following Chemical Formula 1-5; and
  4) reacting a compound represented by the following Chemical Formula 1-5 with dimethyl sulfate in the presence of a base to prepare a compound represented by the following Chemical Formula 1:

[Chemical Formula 1]

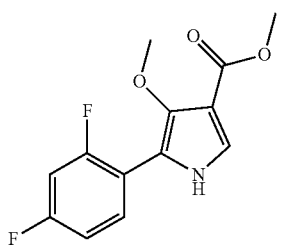

[Chemical Formula 1-1]

[Chemical Formula 1-2]

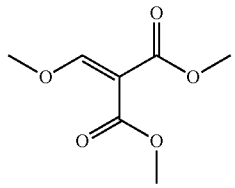

[Chemical Formula 1-3]

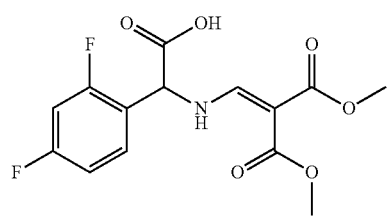

[Chemical Formula 1-4]

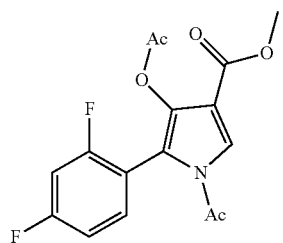

[Chemical Formula 1-5]

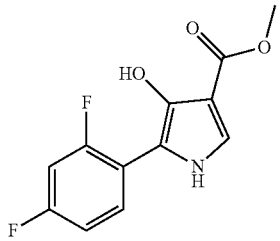

2. The method according to claim 1, wherein the molar ratio of the compound represented by the Chemical Formula 1-1 to the compound represented by the Chemical Formula 1-2 in the step 1 is 10:1 to 1:10.

3. The method according to claim 1, wherein a reaction solvent in the step 1 is an alcohol having 1 to 4 carbon atoms.

4. The method according to claim 1, wherein the reaction temperature in the step 1 is 60 to 100° C.

5. The method according to claim 1, wherein the molar ratio of the compound represented by the Chemical Formula 1-3 to acetic anhydride in the step 2 is 1:1 to 1:32.

6. The method according to claim 1, wherein the reaction temperature in the step 2 is 70 to 100° C.

7. The method according to claim 1, wherein the molar ratio of the compound represented by the Chemical Formula 1-3 to the base in the step 2 is 1:1 to 1:10.

8. The method according to claim 1, wherein a solvent for the reaction of the step 2 is acetonitrile, or tetrahydrofuran.

9. The method according to claim 1, wherein the base of the step 3 is sodium hydroxide.

10. The method according to claim 1, wherein the molar ratio of the compound represented by the Chemical Formula 1-4 to the base in the step 3 is 1:1 to 1:10.

11. The method according to claim 1, wherein a solvent for the reaction in step 3 is an alcohol having 1 to 4 carbon atoms.

12. The method according to claim 1, wherein the reaction temperature in the step 3 is −45 to 5° C.

13. The method according to claim 1, wherein the molar ratio of the compound represented by the Chemical Formula 1-5 to dimethyl sulfate in the step 4 is 1:1 to 1:10.

14. The method according to claim 1, wherein a solvent for the reaction in the step 4 is an alcohol having 1 to 4 carbon atoms or a ketone having 3 to 6 carbon atoms.

15. The method according to claim 1, wherein the reaction temperature in the step 4 is −5 to 10° C.

* * * * *